United States Patent [19]

Paul

[11] Patent Number: 5,089,632
[45] Date of Patent: Feb. 18, 1992

[54] PROCESS FOR PREPARING CYCLIC ESTERS USING A FLUOROCARBON

[75] Inventor: Donald C. Paul, Landenberg, Pa.

[73] Assignee: E. I. Du Pont de Nemours and Company, Wilmington, Del.

[21] Appl. No.: 648,003

[22] Filed: Jan. 30, 1991

[51] Int. Cl.$^5$ .................................. C07D 319/12
[52] U.S. Cl. ...................................... 549/274
[58] Field of Search ................................ 549/274

[56] References Cited

U.S. PATENT DOCUMENTS

| | | | |
|---|---|---|---|
| 1,095,205 | 5/1914 | Gruter et al. | 549/274 |
| 2,668,162 | 2/1954 | Lowe | 260/78.3 |
| 2,703,316 | 3/1955 | Schneider | 260/78.3 |
| 3,878,284 | 4/1975 | Schmitt et al. | 264/184 |
| 4,033,938 | 7/1977 | Augurt et al. | 549/274 |
| 4,727,163 | 2/1988 | Bellis | 549/274 |
| 4,797,468 | 1/1989 | De Vries | 549/274 |
| 4,835,293 | 5/1989 | Bhatia | 549/274 |
| 4,880,219 | 11/1989 | Murdoch et al. | 525/413 |
| 4,895,681 | 1/1990 | Herrmann et al. | 260/410 |
| 4,966,982 | 10/1990 | Ono et al. | 549/274 |
| 4,983,745 | 1/1991 | Muller et al. | 549/274 |
| 4,990,222 | 2/1991 | Aigner et al. | 203/91 |

FOREIGN PATENT DOCUMENTS

| | | |
|---|---|---|
| 3632103 | 3/1988 | Fed. Rep. of Germany . |
| 3708915 | 9/1988 | Fed. Rep. of Germany . |
| 9001521 | 2/1990 | World Int. Prop. O. . |

*Primary Examiner*—C. Warren Ivy
*Assistant Examiner*—Amelia Owens
*Attorney, Agent, or Firm*—Charles E. Krukiel; Michael K. Boyer

[57] ABSTRACT

Process for preparing high purity solvent-free cyclic esters from alpha hydroxycarboxylic acids via an intermediate oligomer wherein a fluorocarbon or a mixture of fluorocarbons is employed to strip the ester from the oligomer as well as a refrigerant to quench lactide from a gaseous reaction stream comprising, besides cyclic ester, unconverted alpha-hydroxycarboxylic acid and water.

18 Claims, 1 Drawing Sheet

PROCESS FOR PREPARING CYCLIC ESTERS USING A FLUOROCARBON

FIELD OF THE INVENTION

The invention relates to a process for preparing high purity solvent-free cyclic esters from alpha-hydroxycarboxylic acids via an intermediate oligomer wherein a fluorocarbon or a mixture of fluorocarbons is employed as a refrigerant to quench lactide from a gaseous reaction stream comprising, besides cyclic ester, unconverted alpha-hydroxycarboxylic acid and water. The invention further relates to a fluorocarbon-assisted process for the rapid production of solvent free cyclic ester such as lactide starting with an alpha-hydroxycarboxylic acid, such as lactic acid, and continuing through oligomer formation, its depolymerization and recovery.

BACKGROUND OF THE INVENTION

The preparation of cyclic esters of alpha-hydroxycarboxylic acids such as lactide is an old and much studied process. These esters have generally been prepared by polymerizing the desired acid (lactic acid) to a relatively low molecular weight oligomer (oligomeric polylactic acid), then heating the oligomer, generally in the presence of a catalyst, to depolymerize it to the cyclic ester (lactide) which is recovered as a component of a vapor product stream.

Such a process suffers in that long reaction times and high temperatures are involved. The long residence times at high temperatures employed often results in side reactions, leading to unwanted isomers, charring of the polymer and yield loss.

An improvement over the processes of the prior art is found in U.S. Pat. No. 4,835,293, which discloses a depolymerization process for the production of lactide wherein "an inert gas, preferably nitrogen" (col. 3, line 33) is fed into a reactor so that the lactide vapors are carried out from the reaction zone along with the nitrogen. The resulting gaseous product stream is scrubbed with a polar organic solvent to recover the lactide.

In the process to manufacture the highly valuable, pure L-lactide, use of an alcoholic or aqueous solvent as a scrubber liquid for the recovery of the L-lactide from the vapor product is not entirely satisfactory. Lactide reacts in the alcoholic solution to form alkyl lactate, which not only constitutes a yield loss but further increases the solubility of all lactide in the scrubbing solution, further aggravating the yield loss problem. Also, in the manufacture of pure optical dimers such as L-lactide, the starting L-lactic acid used to make lactide always contains some D-lactic acid. Therefore, the lactide reaction product always contains some meso-isomer. Meso-lactide is more soluble in alcohol than L-lactide and concentrates in the alcohol. This, in turn, tends to increase the solubility of the L-isomer in the alcohol further increasing the yield loss. Thus, when the desired L-lactide, unreacted L-lactic acid and other lactic acid values are recovered from the alcoholic filtrate, which is normally recycled to the oligomer production portion of the process, they are accompanied by the meso lactide, which continues to build up in the system and eventually results in greater solubility losses of L-lactide and decreased efficiency of the process.

On the other hand, use of non-hydroxylic scrubbing solvents such as acetone, for example, which are non-reactive towards lactide and in which lactides are highly soluble, likewise presents difficulties inasmuch as such polar solvents solubilize the by-product hydroxycarboxylic acids causing them to be incorporated in the lactide product which would require further processing to separate the lactide from the acids.

Water as a scrubbing solvent is also unsatisfactory in that heat transfer to the water from the lactide is much faster than mass transfer; consequently, lactide precipitates as fog of particles which are difficult to capture in the absence of specialized and costly equipment.

Thus a need exists for a process of producing solvent-free lactide in the absence of a polar organic solvent in good yields without use of expensive equipment.

It is an object of this invention to provide a process that meets this need. It is a further object to provide an improved low temperature gas-assisted process, with low residence times and at high conversion rates for converting lactic acid to lactide via its oligomer at a high production rate and good yield using a fluorocarbon as a gas-stripping agent and as a quench solvent to remove lactide polymers, oligomers and dimers from a gas stream containing same.

SUMMARY OF THE INVENTION

A fluorocarbon-assisted process for preparing high purity solvent-free cyclic esters having the formula

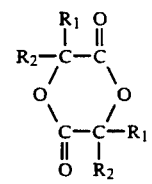

wherein $R_1$ and $R_2$ are independently a hydrogen or an aliphatic hydrocarbyl radical having 1 to 6 carbon atoms, comprises heating an alpha-hydroxycarboxylic acid to form an oligomer, feeding said oligomer into a reaction zone maintained at a temperature sufficient to depolymerize the oligomer and form cyclic ester, feeding into the reaction zone a fluorocarbon that is gaseous at said temperature, said fluorocarbon forming a gaseous stream contacting the oligomer so as to form a large interfacial area with the oligomer, said fluorocarbon being fed in an amount sufficient to strip cyclic ester from the oligomer substantially as fast as it is formed; removing the gas stream containing cyclic ester from the reaction zone; and precipitating the cyclic ester from the gas stream by quenching with a liquified fluorocarbon in the absence of a polar organic solvent.

In a preferred embodiment, the fluorocarbon used to strip lactide from oligomer would be the same as the fluorocarbon used to quench the lactide from the gas exiting the reaction zone. Furthermore, the fluorocarbon vaporized in the quench step and exiting the quench step in the vapor state is recycled back to the depolymerizer and/or cyclic ester collecting vessel.

This invention is based on the discovery that solvent-free cyclic ester can be produced by quenching a gas stream containing water, cyclic ester and unconverted acid with a fluorocarbon.

DETAILED DESCRIPTION OF THE INVENTION

Figure 1:
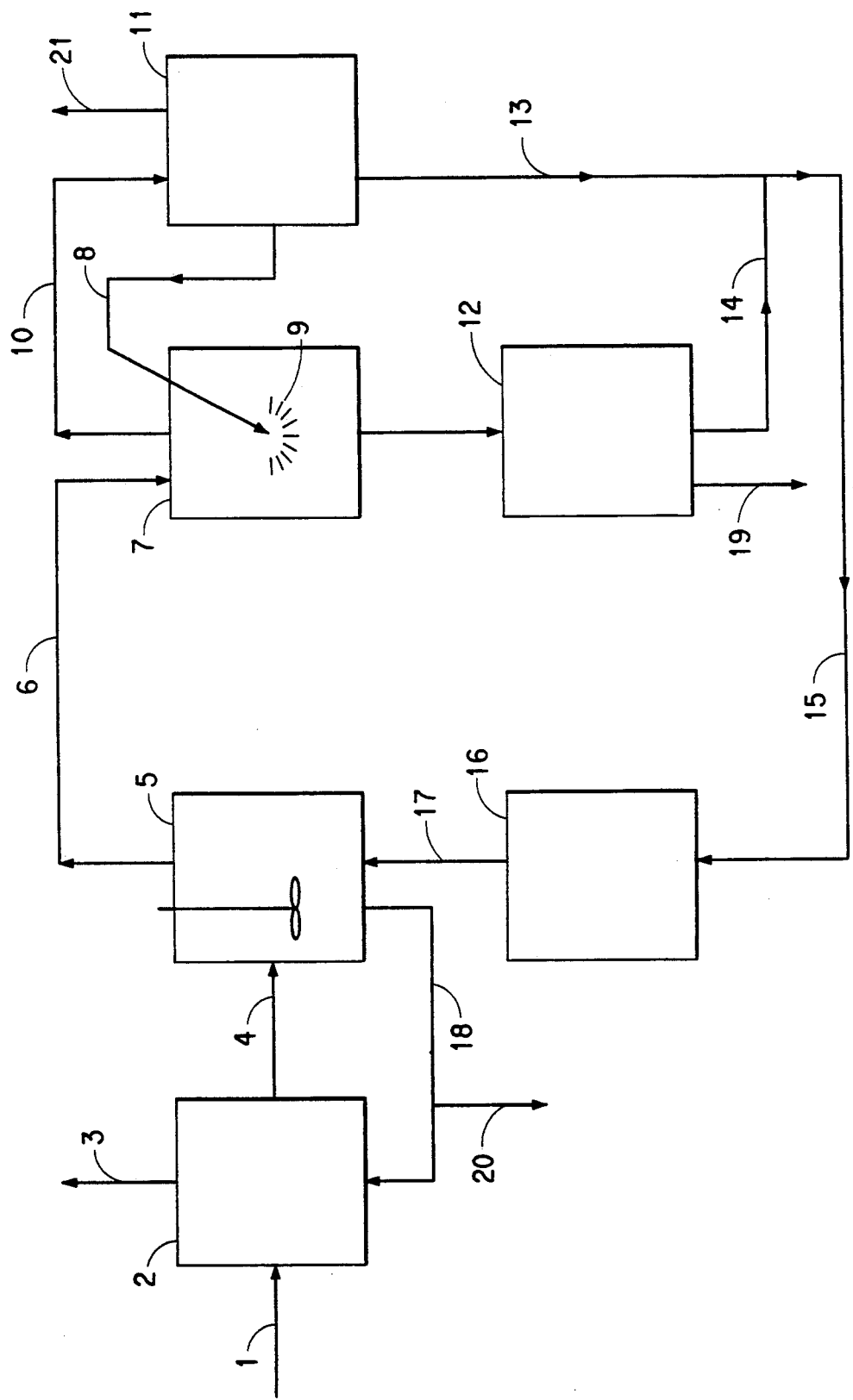
FIG. 1 is a schematic drawing of an apparatus which may be used to practice the process of the invention.

In general, the process is conducted by heating an alpha-hydroxycarboxylic acid oligomer to a temperature effective to depolymerize it to a cyclic ester such as, for example, lactide. At the same time, a gaseous fluorocarbon acting as a stripping agent, and later in the process as a scrubbing solvent, is passed into the liquid reaction mass in an amount and at a rate so as to create a large interfacial area between the fluid reaction mass and the gaseous fluorocarbon, and the amount of gas is sufficient to strip lactide rapidly from the reaction mass. The stripping gas forms a product stream containing lactide and other volatile material that may be present in the incoming feed stream or reaction mass. The product stream is removed from the reaction zone and the lactide is separated from the product stream by quenching the gas stream with a liquid fluorocarbon in the absence of a polar organic solvent which causes the lactide to precipitate. The resulting lactide is solvent free. The portion of fluorocarbon used in the quench process which is vaporized can be collected, and the fluorocarbon stripping gas fed to a condenser, liquefied and reused.

The process of this invention will preferably be conducted in the presence of a catalyst, carried in the feed stream along with the oligomeric reactant or incorporated directly into the reaction mass.

The gaseous agent for entraining/carrying/sweeping the cyclic ester and water of reaction out of the reaction mixture and out of the reactor, as well as for quenching the lactide from the product stream, can be any fluorocarbon that is gaseous and stable at the operating temperatures and pressures, non-toxic, inert to the starting material, reaction mass components and reaction products, and preferably environmentally acceptable. The fluorocarbon may be normally non-gaseous but gaseous at the reaction temperature and pressure. Any of the members of the FREON ® family of fluorocarbon compounds can be used in the present invention. FREON is a registered trademark of E. I. du Pont de Nemours and Company. The FREON ® family includes $CCl_3F$, $CCl_2F_2$, $CClF_3$, $CBrF_3$, $CF_4$, $CHCl_2F$, $CHClF_2$, $CHF_3$, $CCl_2F$-$CCl_2F$, $CCl_2F$-$CClF_2$, $CClF_2$-$CClF_2$, $CClF_2$-$CF_3$ and $CF_3CF_3$.

Preferred are fluorocarbons having low ozone depletion potentials, i.e., less than 1.0, remain gaseous below the condensation temperature of the lactide product, having high refrigeration coefficient of performance (a measure of refrigerant energy efficiency), are readily available at a reasonable price and are capable of being recycled cheaply. From an operational standpoint, the preferred fluorocarbons are those which have vapor pressures of about 1.0 atmospheres or above at operating temperature. Such preferred groups have boiling points below room temperature, preferably at or below zero degree Centigrade. Illustrative of fluorocarbon compounds having such boiling points are FC-124 ($CHClCF_3$), FC-31 ($CH_2ClF$), FC-142b ($CClF_2CH_3$), FC-C318 ($C_4F_8$) and FC-114 ($CClF_2CClF_2$). Their ozone depletion potentials are respectively 0.05, 0.05, 0.05, zero and 0.6.

In a broad sense any fluorocarbon of the formula

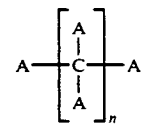

wherein all A's are independently hydrogen, chlorine, or fluorine, at least one being fluorine, and N=1 through 4, can be used, although the HCFC compounds are usually preferred over the CFCs because they are environmentally safer. Table 1 shows a list of chlorofluorocarbon alternatives containing hydrogen.

TABLE 1

| Chlorofluorocarbons | Alternatives |
| --- | --- |
| CFC-11 ($CCl_3F$) | HCFC-123 ($CHCl_2CF_3$) |
| | HCFC-141b ($CH_3CCl_2F$) |
| CFC-12 ($CCl_2F_2$) | HFC-134a ($CH_2FCF_3$) |
| CFC-113 ($CCl_2CCClF_2$) | HCFC-225ca |
| | ($CF_3CF_2CHCl_2$) |
| | HCFC-225cb |
| | ($CHClFCF_2CClF_2$) |
| CFC-114 ($CClF_2CClF_2$) | HCFC-124 ($CHClFCF_3$) |
| CFC-115 ($CClF_2CF_3$) | HFC-125 ($CHF_2CF_3$) |

The following HFCs, in addition to those mentioned in Table 1, are suitable for use as a quenching agent in the invention:

| | |
| --- | --- |
| HFC-32 | $CH_2F_2$ |
| HFC-134 | $HCF_2CF_2F$ |
| HFC-143a | $CF_3CH_3$ |
| HFC-152 | $CH_2F$—$CH_2F$ |
| HFC-152a | $CH_3$—$CHF_2$ |
| HFC-227 EA | $CF_3$—$CHF$—$CF_3$ |
| HFC-356 MFF | $CF_3$—$CH_2$—$CH_2$—$CF_3$ |
| HFC-365 MFC | $CF_3$—$CH_2$—$CF_2$—$CH_3$ |

HFC manufacture is known in the art. See "Aliphatic Fluorine Compounds", H. M. Lovelace et al., 1958, p. 55. For a discussion of fluorocarbons their preparation and use as refrigerants can be found in the Kirk-Othmer Encyclopedia of Chemical Technology, Third Edition, Volume 10, pages 836–870.

While it is customary to use a single fluorocarbon in the practice of this invention, one may employ as an alternative a blend of fluorocarbons such as a blend of the following three fluorocarbons:

| | |
| --- | --- |
| HCFC-22 | ($CHClF_2$), |
| HFC-152a | ($CH_3CHF_2$), and |
| HCFC-124. | |

Such a blend is reported to have a better energy efficiency than either HFC-134a or CFC-12.

Preferably, the fluorocarbon will be injected below the surface of the reaction mass material in the reaction zone; for example, introduced below the agitator of a stirred tank reactor or fed into the bottom of a vertically disposed reactor so that it can counter-currently contact down-flowing oligomer. This technique allows one to run a short residence time continuous reaction.

The flow rate of the fluorocarbon gas should be sufficiently high so as not to limit the cyclic ester stripping rate. If the flow rate is too low, the conversion to lactide may be adversely affected and its production rate limited since the gas functions importantly to carry the lactide as vapor out of the reactor.

Suitably effective temperatures for converting oligomer to cyclic ester can vary widely, but normally will be in the range of from about 185° to 270° C., preferably in the range of from about 190° to 235° C. The optimum temperature for any particular oligomer-to-cyclic ester conversion will vary with composition. For example, for the product of L- or D-lactide the temperature will preferably range from about 190° to 220° C. The higher temperatures are preferably employed for the production of glycolide.

The depolymerization reactor design and configuration are not critical provided there are means for introducing an oligomer feed, means for introducing a cyclic ester-stripping agent, i.e., the fluorocarbon, into the reaction zone such that it directly and intimately contacts the oligomeric composition so as to give high gas-liquid interfacial and has means for removing a gaseous stream containing the lactide.

Thus, the reactor may be a stirred tank equipped with gas-sparging means, preferably one which admits the gas directly under the agitator. The reactor may also be a packed or sieve-plate column, or it may be of any other design known in the art for effecting intimate gas-liquid contact, for example, an atomizer or spray reactor, again with means for introducing the gaseous component such that it intimately contacts the spray of oligomer constituting the reaction mass.

The product lactide is removed from the reactor fluorocarbon sweep gas by contacting the gas with liquid fluorocarbon. The cool liquid fluorocarbon contacts the hot lactide-containing gas stream at which time the liquid is vaporized. This change in phase produces a cooling effect which reduces the temperature of the combined gas stream sufficiently to cause the lactide in the gas phase to condense. Preferably the amount of liquid fluorocarbon fed to the scrubbing chamber will just balance the amount of energy required to lower the combined gas stream temperature to just below the condensation temperature for lactide in the combined gas stream. It may be desirable to use more liquid fluorocarbon than is required to achieve exactly the temperature in the combined gas stream at which lactide condenses from the gas stream, thus cooling the gas stream to a temperature below the condensation temperature of lactide and making the condensation process more efficient.

The scrubbing process can be carried out in any vessel which allows intimate contacting of the liquid fluorocarbon with the reactor sweep gas. This could be a pipe, a tank, a venturi, an orifice or any liquid/gas contacting device which maximizes gas/liquid contact. It is preferred that the liquid fluorocarbon be atomized into small droplets to maximize the rate of vaporization and, in turn, the rate of cooling of the sweep gas stream. Furthermore, the atomized liquid can be introduced in such a way that the droplets initially flow counter-current to the sweep gas flow further maximizing the rate of vaporization and therefore cooling. Any state of the art atomization device would be sufficient including but not limited to spray nozzles or rotary vane atomizers.

It is further desirable to choose a liquid fluorocarbon and liquid fluorocarbon flow rate such that the desired temperature of the combined gases exiting the contacting device is achieved, while at the same time all the liquid fluorocarbon is vaporized, thus producing a dry or semi-dry lactide product.

Furthermore, it is desirable to choose the temperature of the combined gas stream exiting the contacting device such that only the lactide is condensed, allowing all lower boiling, more volatile compounds in the gas stream to remain in the gas stream.

The invention may be better understood with reference to FIG. 1, which schematically depicts several embodiments of the invention involving a lactic acid-to-polylactic acid converter, means for recycling unconverted lactic acid to the converter, a depolymerizer unit for depolymerizing (cracking) polylactic acid to lactide, a gaseous fluorocarbon means for stripping lactide from the depolymerizer and a liquefied fluorocarbon means for precipitating lactide from the resulting gaseous product stream.

In a typical operation, concentrated aqueous lactic acid, preferably containing about 80-90% by weight lactic acid, e.g., 88% acid as is available commercially, is fed through line 1 to the lactic acid-to-oligomer converter 2 where it is further concentrated by distillation and polymerization to lactic acid oligomer, the water of reaction being removed overhead via line 3. The oligomer produced in converter 2 is sent through line 4 to depolymerizer 5, where it is depolymerized under agitation at about 185° to 235° C., preferably 195° to 220° C. with a flow of gaseous fluorocarbon from line 17 being introduced into the depolymerizer 5. The gaseous product stream containing lactide fluorocarbon gas, minor proportions of lactic acid and water exit the depolymerizer through 6 to lactide collector 7 where liquefied fluorocarbon from condenser 11 is brought into contact with the gaseous product stream through line 8 and atomizer 9 and the lactide is caused to precipitate out. At least a portion of the liquid fluorocarbon is vaporized and exits as a gas along with the gaseous fluorocarbon from the depolymerizer through line 10 which leads to a compressor-condenser system 11 wherein the fluorocarbon gas is compressed, cooled and condensed to a liquid. The solidified lactide and any unvaporized fluorocarbon are transported to vessel 12 from which solid lactide product is separated and removed through line 19 and liquid fluorocarbon is sent from vessel 12 to volatilizer 16 via lines 14 and 15, line 14 merging with line 13. The recycled liquid fluorocarbon is vaporized in volatilizer 16 where the resulting gaseous fluorocarbon exits through line 17 to the depolymerizer 5. Fluorocarbon needed to provide sufficient gaseous material to strip lactide from the oligomer in depolymerizer 5 is provided by condenser 11 feeding vaporizer 16 via lines 13 and 15. Non-condensable materials can be purged from compressor-condenser system 11 through purge line 21.

Any fluorocarbon gas vaporized from lactide vessel 12 can be fed to condenser 11 through vessel 7 through a line not shown. It will be appreciated that the oligomer from lactic acid can be pumped to depolymerizer 5 by a pump not shown. Residual unconverted oligomer in 5 can be recycled to converter 2, via line 18 and if necessary to avoid build up of an undue amount of material in depolymerizer 5, a purge stream can be removed via line 20. Make-up fluorocarbon to replace any fluorocarbon lost from or destroyed by the system can be added to compressor-condenser system 11 through a line not shown.

I claim:

1. In a process for preparing a cyclic ester having the formula:

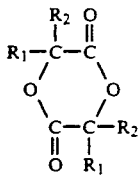

wherein $R_1$ and $R_2$ are independently hydrogen or an aliphatic hydrocarbyl radical having 1 to 6 carbon atoms, by depolymerizing the oligomer resulting from the pyrolysis of an alpha-hydroxycarboxylic acid in a reaction zone, the improvement which comprises sweeping a gaseous fluorocarbon through the so as to create a large interfacial area with the oligomer and so as reaction zone to form a gas product stream comprising at least one member of the following group: water, cyclic ester and unpolymerized alpha-hydroxycarboxylic acid; contacting the gas product stream with a liquefied fluorocarbon, in the absence of an organic polar scrubbing solvent, to precipitate cyclic ester from the gas product stream; vaporizing at least a portion of the liquefied fluorocarbon, and; collecting the cyclic ester which precipitated.

2. In a process for preparing lactide by depolymerizing the oligomer resulting from the pyrolysis of lactic acid in a reaction zone, the improvement which comprises sweeping a gaseous fluorocarbon through the so as to create a large interfacial area with the oligomer and so as reaction zone to form a gas product stream comprising at least one member of the following group: water, lactide and unpolymerized lactic acid; contacting the gas product stream with a liquefied fluorocarbon, in the absence of an organic polar scrubbing solvent to precipitate lactide from the gas product stream; vaporizing at least a portion of the liquified fluorocarbon, and; collecting the lactide which precipitated.

3. The process of claim 1 wherein any fluorocarbon exiting the process in the vapor phase is condensed to its liquid state and recycled to the contacting step.

4. The process of claim 1 wherein unvaporized fluorocarbon from the contacting step is volatilized to a gas and fed into the reaction zone.

5. The process of claim 2 wherein the liquefied fluorocarbon feed rate to the contacting step is controlled as to result in no residual liquid fluorocarbon in the lactide product.

6. The process of claim 2 wherein the liquefied fluorocarbon is introduced to the contacting step through an atomizing means.

7. The process of claim 6 wherein the flow from the atomizing means is directed counter-current to the flow of the gas product stream from the reaction zone.

8. The process of claim 1 wherein the fluorocarbon comprises at least one compound having the formula

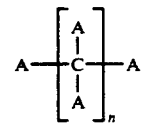

wherein all "A"s are independently hydrogen, chlorine or fluorine, at least one being fluorine and n = 1 through 4.

9. The process of claim 1 wherein said fluorocarbons comprise at least one member of the following group: $CCl_3F$, $CCl_2F_2$, $CClF_3$, $CBrF_3$, $CF_4$, $CHCl_2F$, $CHClF_2$, $CHF_3$, $CCl_2F-CCl_2F$, $CCl_2F-CClF_2$, $CClF_2-CClF_2$, $CClF_2CF_3$ and $CF_3CF_3$.

10. The process of claim 1 wherein said fluorocarbons possess a vapor pressure of at least about 1.0 atmosphere.

11. The process of claim 1 wherein said fluorocarbons possess a low ozone depletion potential.

12. The process of claim 1 wherein said fluorocarbons comprise $CClF_2CClF_2$.

13. The process of claim 1 wherein said fluorocarbons comprise $CH_2FCF_3$.

14. The process of claim 1 wherein said fluorocarbons comprise $CHClFCF_3$.

15. The process of claim 1 wherein said fluorocarbons comprise $CClF_2CH_3$.

16. The process of claim 1 wherein said fluorocarbons comprise $C_4F_8$.

17. The process of claim 1, wherein said fluorocarbons comprise a blend of HCFC-22, HFC-152a and HCFC-124.

18. The process of claim 1, wherein the fluorocarbon which is used in the sweeping step and the liquefied fluorocarbon comprises a fluorocarbon blend.

* * * * *